(12) United States Patent
Kon et al.

(10) Patent No.: US 9,040,295 B2
(45) Date of Patent: *May 26, 2015

(54) ANTI-HUMAN α9 INTEGRIN ANTIBODY AND USE THEREOF

(71) Applicant: GENE TECHNO SCIENCE CO., LTD., Chuo-ku, Sapporo-shi, Hokkaido (JP)

(72) Inventors: Shigeyuki Kon, Hokkaido (JP); Toshimitsu Uede, Hokkaido (JP)

(73) Assignee: Gene Techno Science Co., Ltd., Hokkaido (JP)

( * ) Notice: Subject to any disclaimer, the term of this patent is extended or adjusted under 35 U.S.C. 154(b) by 79 days.

This patent is subject to a terminal disclaimer.

(21) Appl. No.: 13/742,680

(22) Filed: Jan. 16, 2013

(65) Prior Publication Data

US 2013/0122019 A1   May 16, 2013

Related U.S. Application Data

(63) Continuation of application No. 13/138,470, filed as application No. PCT/JP2009/053218 on Feb. 23, 2009.

(51) Int. Cl.
| A61K 39/395 | (2006.01) |
| C07K 16/00 | (2006.01) |
| C07K 16/28 | (2006.01) |

(52) U.S. Cl.
CPC ......... C07K 16/2839 (2013.01); *C07K 2317/76* (2013.01); *G01N 2333/70546* (2013.01)

(58) Field of Classification Search
None
See application file for complete search history.

(56) References Cited

U.S. PATENT DOCUMENTS

| 7,595,045 B2 * | 9/2009 | Kurotaki et al. | 424/130.1 |
| 8,221,754 B2 * | 7/2012 | Kanayama et al. | 424/139.1 |
| 8,715,655 B2 * | 5/2014 | Torikai et al. | 424/130.1 |
| 2006/0002923 A1 | 1/2006 | Uede et al. | |

FOREIGN PATENT DOCUMENTS

| CN | 1688604 A | 10/2005 |
| EP | 1 840 135 A1 | 10/2007 |
| EP | 2 048 163 A1 | 4/2009 |
| WO | WO 02/081522 A1 | 10/2002 |
| WO | WO 2006/075784 A1 | 7/2006 |
| WO | WO 2008/007804 A1 | 1/2008 |
| WO | WO 2008/081522 A1 | 7/2008 |

OTHER PUBLICATIONS

Kanayama et al. α9 Integrin and Its Ligands Constitute Critical Joint Microenvironments for Development of Autoimmune Arthritis. The Journal of Immunology Jun. 15, 2009, 182(12):8015-8025.*

Wang et al., "Differential Regulation of Airway Epithelial Integrins by Growth Factors," Am. J. Respir. Cell Mol. Biol., 1996, 15:664-672.

Ota et al. "Tumor-α9β1 integrin-mediated signaling induces breast cancer growth and lymphatic metastasis via the recruitment of cancer-associated fibroblasts," J. Mol. Med., Aug. 1, 2014, XP055145652, ISSN: 0946-2716, DOI: 10.1007/s00109-014-1183-9, 11 pages.

Yokosaki et al., "The Integrin $\alpha_9\beta_1$ Binds to a Novel Recognition Sequence (SVVYGLR) in the Thrombin-cleaved Amino-terminal Fragment of Osteopontin," The Journal of Biological Chemistry, Dec. 17, 1999, 274(51):36328-36334.

* cited by examiner

*Primary Examiner* — Maher Haddad

(74) *Attorney, Agent, or Firm* — Foley & Lardner LLP

(57) ABSTRACT

The present invention relates to an anti-human α9 integrin antibody. More particularly, the present invention relates to: a monoclonal antibody, a chimeric antibody, a humanized antibody and a human antibody that specifically recognize human α9 integrin; a hybridoma cell that produces the monoclonal antibody; a method for producing the monoclonal antibody; a method for producing the hybridoma cell; a therapeutic agent comprising the anti-human α9 integrin antibody; a diagnostic agent comprising the human α9 integrin antibody; and a method for screening for a compound that inhibits the activity of human α9 integrin.

5 Claims, 4 Drawing Sheets

Fig. 1A

Anti-human α9 integrin antibody Heavy chain CDR

K33N

GTS      1: -VKLQESGPELVKPGASVKISCKASGYSFTSYYMNWVKKRPGQGLEWIGW 50

JN Bio   1: QVQLQQSGPELVKPGASVKISCKASGYSFTSYYMNWVKKRPGQGLEWIGW 50

GTS     51: IFPGSGNTKYNEKFKGKATLTADTSSSTAYMQVSSLTSEDSAVYFCARSW 100

JN Bio  51: IFPGSGNTKYNEKFKGKATLTADTSSSTAYMQVSSLTSEDSAVYFCARSW 100

GTS    101: VSYERGYYFDYWCQGTTLTVSS 122

JN Bio 101: VSYERGYYFDYWGQGTSLTVSS 122

M35A

GTS      1: VKLQESGTKLVKPGASVRLSCKASGYTFTSYWIH-WVKQSPGQGLEWIGEI 50

Takara   1: VKLQESGTKLVKPGASVRLSCKASGYTFTSYWIH-WVKQSPGQGLEWIGEI 50

GTS     51: NPSSGRTNFIENFETKATLTVDRSSTTAYMQLT-SLTSEDSAVYYCARLAY 100

Takara  51: NPSSGRTNFIENFETKATLTVDRSSTTAYMQLT-SLTSEDSAVYYCARLAY 100

GTS    101: GNYSW----FAYWGQGTTVTVSS 119

Takara 101: GNYSW----FAYWGQGTTVTVSS 119

Fig. 1B

Anti-human α9 integrin antibody Light chain CDR

K33N

GTS     1: DIQMTQSPASLAASVGETVTLTC<u>RASENIYYSLA</u>WYQQKQGKSPQLLIY<u>N</u>

JN Bio  1: DIQMTQSPASLAASVGETVTLTC<u>RASENIYYSLA</u>WYQQKQGKSPQLLIY<u>N</u> 50

GTS    51: <u>ANSLEDG</u>VPSRFSGSGSGTQYSMKINSMQPEDTATYFC<u>KQAYDVPYTFGG</u> 100

JN Bio 51: <u>ANSLEDG</u>VPSRFSGSGSGTQYSMKINSMQPEDTATYFC<u>KQAYDVPYTFGG</u> 100

GTS   101: GTKLELK

JN Bio 101: GTKLEIK

M35A

GTS     1: QIVLTQSPASLAVSLGQRATISC<u>RASETVDSYGNTFMH</u>WYQQKPGQPPKL 50

Takara  1: DIVLTQSPASLAVSLGQRATISC<u>RASETVDSYGNTFMH</u>WYQQKPGQPPKL 50

GTS    51: LIY<u>LASNLES</u>GVPVRFSGSGSRTDFTLTIDPVEADDAATYYC<u>QQNNED-PY</u> 100

Takara 51: LIY<u>LASNLES</u>GVPVRFSGSGSRTDFTLTIDPVEADDAATYYC<u>QQNNED-PY</u>

GTS   101: TFGGGTNWKNGR 112

Takara 101: TFGGGTKLEIKR 112

ANTI-HUMAN α9 INTEGRIN ANTIBODY AND USE THEREOF

CROSS-REFERENCE TO RELATED APPLICATIONS

This application is a Continuation of U.S. application Ser. No. 13/138,470, issued as U.S. Pat. No. 8,372,639, which is the US National Stage application of PCT/JP2009/053218, filed Feb. 23, 2009. The entire contents of each of the aforementioned applications are incorporated herein by reference.

The instant application contains a Sequence Listing which has been submitted in ASCII format via EFS-WEB and is hereby incorporated by reference in its entirety. Said ASCII copy, created on Jan. 14, 2013, is named sequence.txt and is 23 KB.

TECHNICAL FIELD

The present invention relates to an anti-human α9 integrin antibody and use thereof. More particularly, the present invention relates to: a monoclonal antibody, a chimeric antibody, a humanized antibody and a human antibody that specifically recognize human α9 integrin; a hybridoma cell that produces the monoclonal antibody; a method for producing the monoclonal antibody; a method for producing the hybridoma cell; a therapeutic agent comprising the anti-human α9 integrin antibody; a diagnostic agent comprising the anti-human α9 integrin antibody; and a method for screening for a compound that inhibits the activity of human α9 integrin.

BACKGROUND ART

Adhesion between a cell and the extracellular matrix is mediated by a transmembrane cell adhesion protein as typified by integrins. Integrins are heterodimers that have 1:1 of α- and β-chains. So far, 18 types of α-chains and 8 types of β-chains have been found where at least 24 types of combinations thereof have been identified and confirmed. Each integrin is known to recognize a specific extracellular matrix (ligand). Moreover, the transmembrane cell adhesion protein containing an integrin not only plays a role of adhering and anchoring a cell and the extracellular matrix but it has also been found to convert information from the extracellular matrix into intracellular signals for regulating cell proliferation, motility, cell death, differentiation and the like.

Integrins are classified, according to their specificities and functions with respect to ligands, into subfamilies, namely, collagen receptors, laminin receptors, RGD receptors that recognize Arg-Gly-Asp (RGD) sequence contained in fibronectin, vitronectin and the like, and leukocyte-specific receptors that exist only in leukocytes. Alpha-4 integrins and α9 integrins do not belong to any of these subfamilies and are called α4 integrin subfamily.

Ligands that are known to bind to α4 and α9 integrins include osteopontin (hereinafter, referred to as OPN), EDA domain of fibronectin, propeptide-von Willebrand factor (pp-vWF), tissue transglutaminase (tTG), coagulation factor XIII and Vascular Cell Adhesion Molecule-1 (VCAM-1). Furthermore, ligands that are known to be recognized specifically by α4 integrin include CS-1 domain of fibronectin, MadCAM-1 (α4β7) and the like. Meanwhile, ligands that are known to be recognized specifically by α9 integrin include tenascin C, plasmin and the like.

OPN, one type of extracellular matrices (ECM), is a secreted acid phosphorylated acid glycoprotein with a molecular weight of about 41 kDa, which is a molecule generally acknowledged to be expressed in breast milk, urine, renal tubules, osteoclasts, osteoblasts, macrophage, activated T cell, tumor tissue and the like. OPN has cell adhesion sequence GRGDS (SEQ ID NO:17) in the middle, and SVVYGLR (SEQ ID NO:18) or SLAYGLR (SEQ ID NO:19) sequence for human or murine OPN, respectively, which is immediately followed by a thrombin cleavage site. OPN adheres to integrin of RGD receptor via the GRGDS sequence (SEQ ID NO:17) and to α4 (α4β1) and α9 (α9β1) integrins via the SVVYGLR sequence (SEQ ID NO:18) or the SLAYGLR sequence (SEQ ID NO:19).

While α4β1 binds to OPN that is not cleaved with thrombin (non-cleaved OPN) as well as an N-terminal fragment cleaved with thrombin (cleaved OPN), α9β1 differs in that it binds only to cleaved OPN.

The amino acid sequences of α4,α9 and β1 integrin subunits are known and are registered with GenBank. The amino acid sequences are known to be highly similar among the species.

WO02/081522 discloses a therapeutic effect for rheumatoid arthritis and hepatitis by utilizing an OPN-deficient mouse and a neutralizing antibody against OPN to suppress the OPN functions. This publication also discloses that the SVVYGLR sequence (SEQ ID NO:18), i.e., a sequence that recognizes α4 and α9 integrins, plays an important role upon onset of an inflammatory disease and that a receptor for OPN involved in inflammatory diseases is expressed in the immunocompetent cell or the like.

DISCLOSURE OF THE INVENTION

Problems to be Solved by the Invention

Currently, various therapeutic drugs for cancers, inflammatory diseases, infectious diseases, autoimmune diseases and bone diseases are known but development of a prophylactic drug and/or a therapeutic drug with improved therapeutic effects for cancers, inflammatory diseases, infectious diseases, autoimmune diseases and bone diseases are desired.

Until today, the present inventors have conducted various studies focusing on integrins, in particular α9 integrin. As a result, they found that an antibody that specifically inhibits α9 integrin has a cancer suppressing effect as well as an anti-inflammatory effect and produced five types of hybridoma cells that produces the monoclonal antibody (1K11, 21C5, 24I11, 25B6 and 28S1) (each deposited with the International Patent Organism Depositary, the National Institute of Advanced Industrial Science and Technology (Central 6, Higashi 1-1-1, Tsukuba-shi, Ibaraki-ken, 305-8566) as FERM BP-10510, FERM BP-10511, FERM BP-10512, FERM BP-10513 and FERM BP-10832, respectively (the first four cells deposited on Feb. 15, 2006 and the last one on May 29, 2007)).

Under such circumstances, there has been a need for a monoclonal antibody or an alternative monoclonal antibody with higher drug efficacy.

Means for Solving the Problem

In order to develop a monoclonal antibody or an alternative monoclonal antibody that has superior drug efficacy over the above-mentioned five monoclonal antibodies, the present inventors have gone through keen studies and succeeded in producing a hybridoma cell that produces such a novel monoclonal antibody, thereby accomplishing the present invention.

Thus, the present invention provides an anti-human α9 integrin antibody, a monoclonal antibody thereof, a cell that produces the antibody, a therapeutic agent comprising the antibody, and a method for screening for a compound that inhibits α9 integrin activity.

(1) An anti-human α9 integrin antibody comprising an amino acid sequence represented by any one of SEQ ID NOS:1-12.

(2) An anti-human α9 integrin antibody comprising an amino acid sequence represented by SEQ ID NO:1, 3, 5, 7, 9 or 11.

(3) An anti-human α9 integrin antibody comprising amino acid sequences represented by SEQ ID NOS:1, 3, 5, 7, 9 and 11.

(4) An anti-human α9 integrin antibody comprising an amino acid sequence represented by SEQ ID NO:2, 4, 6, 8, 10 or 12.

(5) An anti-human α9 integrin antibody comprising amino acid sequences represented by SEQ ID NOS:2, 4, 6, 8, 10 and 12.

(6) An anti-human α9 integrin antibody comprising the amino acid sequence represented by any one of SEQ ID NOS:1-6 as an amino acid sequence of the complementary determining region of the heavy chain (CDRH) and the amino acid sequence represented by any one of SEQ ID NOS:7-12 as an amino acid sequence of the complementary determining region of the light chain (CDRL).

(7) The anti-human α9 integrin antibody according to any one of (1)-(6) above, wherein the binding between the human α9 integrin and the ligand of α9 integrin is inhibited.

(8) The anti-human α9 integrin antibody according to any one of (1)-(7) above, wherein it is a monoclonal antibody.

(9) The anti-human α9 integrin antibody according to any one of (1)-(8) above, wherein it is a chimeric antibody.

(10) The anti-human α9 integrin antibody according to any one of (1)-(8) above, wherein it is a humanized antibody.

(11) The anti-human α9 integrin antibody according to any one of (1)-(8) above, wherein it is a human antibody.

(12) An anti-human α9 integrin antibody produced by a hybridoma cell assigned Accession No. FERM BP-10830 or FERM BP-10831.

(13) A therapeutic agent for a cancer, an inflammatory disease, an infectious disease, an autoimmune disease or a bone disease, comprising the anti-human α9 integrin antibody according to any one of (1)-(12) above as an active component.

(14) A therapeutic agent for a cancer, an inflammatory disease, an infectious disease, an autoimmune disease or a bone disease, comprising the anti-human α9 integrin antibody according to any one of (1)-(12) above as well as an anti-human α4 integrin antibody as active components.

(15) A diagnostic agent for a cancer, an inflammatory disease, an infectious disease, an autoimmune disease or a bone disease, comprising the anti-human α9 integrin antibody according to any one of (1)-(12) above as an active component.

(16) A cell that produces the anti-human α9 integrin antibody according to any one of (1)-(12) above.

(17) A hybridoma cell assigned Accession No. FERM BP-10830 or FERM BP-10831.

(18) A method for screening for a compound that inhibits an activity of α9 integrin, comprising using a peptide comprising the amino acid sequence of α9 integrin.

Effect of the Invention

The present invention provides a novel anti-α-integrin antibody. The anti-α9-integrin antibody of the present invention shows an excellent suppression effect against a function of α9 integrin and exerts a therapeutic effect against cancers (for example, cancer cell proliferation or metastasis), inflammatory diseases (for example, rheumatoid arthritis, osteoarthritis, hepatitis, bronchial asthma, fibrosis, diabetes, arterial sclerosis, multiple sclerosis, inflammatory bowel diseases (ulcerative colitis, Crohn's disease, etc.)), infectious diseases (for example, hepatitis), autoimmune diseases (for example, systemic lupus erythematosus, polymyositis, autoimmune thyroid disease, tubulointerstitial nephritis, myasthenia gravis), bone diseases (for example, osteoporosis) and the like. Moreover, a pharmaceutical composition comprising the anti-α9-integrin antibody of the present invention as well as the anti-α4-integrin antibody exerts an improved therapeutic effect against cancers, inflammatory diseases and the like. The antibody of the present invention may also be utilized as a diagnostic drug since it is capable of pathologically detecting expression of α9 integrin in cells and tissues.

MODES FOR CARRYING OUT THE INVENTION

Background of the Invention

Tysabri (registered trademark) (natalizumab), an antibody against α4 integrin, from Biogen Idec Inc. (Massachusetts, USA) and Elan Corporation (Ireland), was approved as a drug for multiple sclerosistherapeutic by the Food and Drug Administration (FDA) in November 2004. Furthermore, Tysabri (registered trademark) is undergoing clinical development directing at diseases such as Crohn's disease and rheumatoid arthritis. An anti-human α4β1 integrin monoclonal antibody, called P4C2, is used in the laboratory.

Although a monoclonal antibody named Y9A2 that shows specificity to human and guinea pig α9 integrins (A. Wang et al, (1996) Am. J. Respir.,Cell Mol. Biol. 15, 664-672) has been subjected to experiments as an antibody against α9 integrin, its clinical use has not yet been realized.

According to the present invention, a novel antibody against human α9 integrin, which is expected to have superior drug efficacy, was obtained by carefully pursuing the following procedures.

(1) Production of Human α9 Integrin Overexpressing Strain

In order to produce an antibody against α9 integrin, gene transfection of mouse fibroblast NIH-3T3 cell was performed to establish a cell line that overexpresses human α9 integrin. This cell line is used as an antigen for immunizing mice.

(2) Screening for Hybridoma

In order to efficiently obtain clones that react exclusively to human α9 integrin from various hybridoma resulting from cell fusion, human α4 integrin belonging to the same integrin family is expressed in CHO-K1 cells. The resulting cells are used to select clones that do not show cross reactivity with other integrins and that do not react with the cell surface antigen of the parent cell (CHO-K1), thereby efficiently obtaining an inhibition antibody that reacts specifically to human α9 integrin.

Anti-α9-Integrin Antibody of the Present Invention

The present invention provides a monoclonal antibody against human α9 integrin. According to the present invention, the term "antibody" refers to the whole antibody molecule or a fragment thereof (for example, Fab, Fab' or F(ab')$_2$ fragment) that specifically binds to α9 integrin or the partial peptide thereof as an antigen, which may be either a polyclonal antibody or a monoclonal antibody. According to the present invention, the term preferably refers to a monoclonal antibody. The term "antibody" according to the present invention also encompasses a chimeric antibody, a humanized antibody and a human antibody.

According to the present invention, when an antibody "specifically binds" to a certain protein or a fragment thereof, it means that the antibody binds to a particular amino acid sequence of the certain protein or the fragment thereof with substantially higher affinity over other amino acid sequences. Herein, the phrase "substantially high affinity" refers to a level of affinity that is sufficient to distinguish and detect a particular amino acid sequence from other amino acid sequences with a desired measurement device or method. Typically, the phrase refers to binding affinity with an association constant ($K_a$) of at least $10^7 M^{-1}$, preferably at least $10^8 M^{-1}$, more preferably $10^9 M^{-1}$, still more preferably $10^{10} M^{-1}$, $10^{11} M^{-1}$, $10^{12} M^{-1}$ or higher, for example, up to $10^{13} M^{-1}$ or higher.

A "monoclonal antibody" according to the present invention refers to an antibody that is highly specific to recognize a single antigen.

According to the present invention, an "antibody fragment" refers to a part of a whole antibody, namely, an antigen-binding region or a variable region. Examples of antibody fragments include Fab, Fab', F(ab')$_2$ and Fv fragments. These antibody fragments may be produced through a generally known technique such as papain digestion or pepsin digestion of the antibody.

The above-mentioned "chimeric antibody" refers to a chimeric human-mouse antibody obtained by genetically engineering the constant region of the anti-human α9 integrin antibody of the present invention to have the same constant region as that of the human antibody (see European Patent Publication No. EP0125023). A "humanized antibody" refers to an antibody obtained by genetically engineering the primary structure of the anti-human α9 integrin antibody of the present invention to have the corresponding primary structure of a human antibody except for the complementarity determining regions (CDRs) of the H- and L-chains. A "human antibody" refers to a monoclonal antibody produced by using a transgenic animal that has been transferred with a human gene involved in human antibody production (see European Patent Publication No. EP0546073).

More specifically, the present invention provides an anti-human α9 integrin antibody that differs from the conventionally-produced anti-human α9 integrin antibodies. An antibody according to the preferred embodiment of the present invention comprises an amino acid sequence represented by SEQ ID NO:1, 3, 5, 7, 9 or 11. More preferable antibody is an anti-human α9 integrin antibody comprising two or more, three or more, four or more, five or more or six amino acid sequences selected from the group consisting of the amino acid sequences represented by SEQ ID NOS:1, 3, 5, 7, 9 and 11.

Furthermore, an antibody according to another embodiment of the present invention comprises an amino acid sequence represented by SEQ ID NO:2, 4, 6, 8, 10 or 12. More preferable antibody is an anti-human α9 integrin antibody comprising two or more, three or more, four or more, five or more or six amino acid sequences selected from the group consisting of the amino acid sequences represented by SEQ ID NOS:2, 4, 6, 8, 10 and 12.

Particularly preferable antibody of the present invention is an anti-human α9 integrin antibody produced by a hybridoma cell assigned Accession No. FERM BP-10830 or FERM BP-10831.

Hereinafter, production of an anti-α9-integrin monoclonal antibody will be described, although the production of the antibody should not be limited thereto.

Alpha-9 Integrin (Antigen)

Alpha-9 integrin as an antigen used with the present invention may be (1) any cell derived from human or other mammal that expresses α9 integrin or a protein derived from any tissue containing this cell, (2) gene DNA coding for α9 integrin, preferably a recombinant protein in which cDNA is introduced and expressed in a cell line such as a bacterium, an yeast or an animal cell, or (3) a synthetic protein.

Furthermore, α9 integrin of the present invention also comprises a polypeptide having an amino acid sequence of α9 integrin from any type of mammal, particularly preferably a polypeptide having substantially the same amino acid sequence as the amino acid sequence (SEQ ID NO:13) of human α9 integrin.

Here, the phrase "a polypeptide having substantially the same amino acid sequence" refers to a mutant polypeptide having an amino acid sequence with substantially the same biological nature as that of the amino acid sequence of natural α9 integrin, particularly preferably human-derived α9 integrin, where several amino acids, preferably 1-10 amino acids and particularly preferably one to several (for example, 1-5, 1-4, 1-3 or 1-2) amino acids are substituted, deleted and/or modified in said amino acid sequence, as well as a mutant polypeptide having an amino acid sequence having several amino acids, preferably 1-10 amino acids, particularly preferably one to several (for example, 1-5, 1-4, 1-3 or 1-2) amino acids added to the amino acid sequence of natural α9 integrin, particularly preferably human-derived α9 integrin. The polypeptide may also be a mutant polypeptide further having some of such substitution, deletion, modification and addition.

Alpha-9 integrin, particularly human-derived α9 integrin, of the present invention may be produced by appropriately employing a gene recombinant technique as well as a method known in the art such as chemical synthesis, cell culturing, or a modified method thereof.

Examples of methods for producing a mutant polypeptide include site-directed mutagenesis using a synthetic oligonucleotide (gapped duplex approach), introduction of random point mutation using nitrous acid or sulfurous acid treatment, production of a deficient mutant using, for example, Ba131 enzyme or the like, cassette mutagenesis, linker scanning technique, misincorporation technique, mismatch primer technique and synthesis of DNA segment.

In addition, α9 integrin of the present invention also comprises a "part" of said α9 integrin. Herein, the term "part" refers to a portion that includes a region necessary for binding to an α9 integrin ligand such as OPN, tenascin C or VCAM-1. The "part" of said α9 integrin may be produced by a later-described gene recombinant technique or chemical synthesis known in the art or a modified version thereof. Alternatively, it may be produced by appropriately cleaving α9 integrin, particularly preferably human-derived α9 integrin, that has been isolated through cell culturing with protease or the like.

An antigen may also be a cell itself that overexpresses α9 integrin on the cell membrane by recombinant technique, or a membrane fraction or the like thereof.

Alpha-9 integrin of the present invention also comprises a polypeptide having substantially the same amino acid sequence as the amino acid sequence (SEQ ID NO:13) of human α9 integrin. According to the present invention, a cell itself that overexpresses human α9 integrin on the cell membrane by a recombinant technique is particularly preferably used. Hence, a later-described cell that overexpresses human α9 integrin on the cell membrane or a cell membrane fraction thereof may be prepared to be used by itself as an antigen by cloning a gene (for example, cDNA) coding for human α9 integrin according to a known genetic engineering technique.

Preparation of Antibody-Producing Cell

The antigen is administered alone or together with a carrier or a diluent to an animal to be immunized at a site that allows production of the antibody upon administration. In order to enhance the antibody producing capability upon administration, a complete Freund's adjuvant or an incomplete Freund's adjuvant may be administered. The administration takes place generally once in every 1-6 weeks for a total of about 2-10 times. Examples of the warm-blooded animal used include a mouse, monkey, rabbit, dog, guinea pig, rat, hamster, sheep, goat and chicken although a mouse is preferably used in the present invention.

When the subject of the treatment is human and the animal for producing the α9 integrin-inhibiting antibody is a mouse, a chimeric antibody from human and mouse or a humanized antibody is preferably used. Preferably, a transgenic animal such as a mouse that has been introduced with a human gene involved in antibody production is used to produce a humanized monoclonal antibody to be employed.

Cell Fusion of Antibody-Producing Cell and Myeloma Cell

As a myeloma cell, a cell derived from a mouse, rat, human or the like is used. Examples include mouse myeloma P3U1, P3X63-Ag8, P3X63-Ag8-U1, P3NS1-Ag4, SP2/0-Ag14 and P3X63-Ag8-653. Preferably, the antibody-producing cell and the myeloma cell are derived from animals of the same species, particularly animals of the same strain. The myeloma cell may be cryopreserved, or maintained by passage in a general medium supplemented with a fetal horse, rabbit or bovine serum. For cell fusion, cells in logarithmic growth phase are preferably used. According to the present invention, P3X63-Ag8-653 is preferably used.

Examples of a method for fusing the antibody-producing cell and the myeloma cell to form a hybridoma include a method using polyethylene glycol (PEG), a method using Sendai virus, and a method using an electric fusion device. For example, in the case of PEG method, a mixture ratio of 1-10:1, preferably 5-10:1 of spleen cells and myeloma cells are suspended in an appropriate medium or buffer containing about 30-60% of PEG (average molecular weight: 1000-6000) to allow reaction at a temperature of about 25-37° C. under conditions of pH6-8 for about 30 seconds to about 3 minutes. At the end of the reaction, the PEG solution is removed and the resultant is resuspended in a medium and seeded in a cell well plate to continue the culturing.

Sorting of Hybridoma Cells

A hybridoma cell that produces the monoclonal antibody can be sorted according to a known method or a method corresponding thereto. In general, sorting can be performed in a medium for animal cells supplemented with HAT (hypoxanthine, aminopterin, thymidine). The medium used for sorting and breeding may be any medium as long as it allows growth of the hybridoma cell. For example, a RPMI 1640 medium containing 1-20%, preferably 10-20% fetal bovine serum, a GIT medium (Wako Pure Chemical Industries, Ltd.) containing 1-10% fetal bovine serum, or a serum-free medium for culturing hybridoma (SFM-101, Nissui Pharmaceutical Co., Ltd.) can be used. The temperature for culturing is generally 20-40° C., and preferably about 37° C. The time for culturing is generally 5 days to 3 weeks, and preferably 1-2 weeks. In general, culturing may be carried out under 5% $CO_2$.

Production of a monoclonal antibody of the present invention may be confirmed and screened by employing a cellular ELISA technique described in *New Experimental Methods of Clinical Immunology* (*part* 3), Kagaku Hyoron-sha, 1997. When the cell used for immunization is used for screening, the background or the false positives may be expected to increase. In this case, a clone that reacts with human α9 integrin overexpressed in a cell other than the cell used for immunization, but that does not react with a cell that overexpresses human α4 integrin, may be used as an anti-human α9 integrin antibody. Limiting dilution method can be repeated once to five times, preferably twice to four times, on such a clone to prepare a monoclonal antibody.

Separation and Purification of Antibody

The resulting antibody may be purified to homogeneity. Separation and purification of the antibody may be performed by employing a separation and purification technique that is generally used for proteins. For example, but without limitation, a chromatography column such as affinity chromatography, a filter, ultrafiltration, salting-out, dialysis, SDS polyacrylamide gel electrophoresis, isoelectric point electrophoresis or the like may appropriately be selected or combined to separate and purify the antibody (*Antibodies: A Laboratory Manual*. Ed Harlow and David Lane, Cold Spring Harbor Laboratory, 1988). Examples of a column used for affinity chromatography include protein A column and protein G column. For example, a column using a protein A column may be Hyper D, POROS and Sepharose F. F. (Amersham Biosciences).

Labeling of Antibody

The resulting antibody can be labeled according to various labeling (for example, biotin label, FITC label, APC label) by a known method or with commercially available kit. Preferably, a biotin label using Biotin labeling kit (Dojindo Laboratories) is used in the present invention.

The thus-obtained monoclonal antibody is purified, if necessary, and then formulated according to a common technique to be used as a prophylactic and/or therapeutic agent for cancers, inflammatory diseases, infectious diseases, autoimmune diseases and bone diseases. A formulation of these prophylactic and/or therapeutic agents may be a parenteral formulation such as an injectable agent or drip, or may be devised for use as an oral formulation. For formulation, a carrier, a diluent, an additive or the like suitable for the formulation may be used within a medically and pharmaceutically acceptable range.

Pharmacological Effect of Antibody

Integrin not only plays a role of attaching and anchoring a cell and the extracellular matrix (ECM), but also been found to take a role in converting information from the extracellular matrix into intracellular signals for regulating cell proliferation, motility, cell death, differentiation and the like. Since the resulting monoclonal antibody can interrupt the intracellular signaling of information from ECM by inhibiting the binding between ECM and α9 integrin, it can treat ECM-related diseases. Examples of ECM and α9 ligands that are known to bind to α9 integrin include OPN, fibronectin, propeptide-von Willebrand factor (pp-vWF), tissue transglutaminase (tTG), coagulation factor XIII, Vascular Cell Adhesion Molecule-1 (VCAM-1), tenascin C and plasmin. Cells or cancer cells expressing these ECM and α9 integrins are used to observe binding inhibition in vitro in the presence of the resulting monoclonal antibody, thereby determining a disease targeted by the monoclonal antibody of the present invention.

Pharmaceutical Agent Comprising Antibody

A formulation comprising an antibody (in particular, a monoclonal antibody) of the present invention as an active component may be used as a therapeutic agent or a prophylactic agent for cancers (for example, proliferation or metastasis of cancer cells), inflammatory diseases (for example, rheumatoid arthritis, osteoarthritis, hepatitis, bronchial asthma, fibrosis, diabetes, arterial sclerosis, multiple sclerosis or inflammatory bowel diseases (ulcerative colitis or Crohn's disease)), infectious diseases (for example, hepatitis), autoimmune diseases (for example, systemic lupus erythematosus, polymyositis, autoimmune thyroid disease, tubulointerstitial nephritis or myasthenia gravis), bone diseases (for example, osteoporosis) and the like.

The dosage differs depending on the subject of administration, the target disease, conditions, the administration route and the like. For example, in the case where it is used for preventing and/or treating a cancer patient, a single dose of generally about 0.01-20 mg/kg weight, preferably about 0.1-10 mg/kg weight and more preferably about 0.1-5 mg/kg weight of the antibody of the present invention is conveniently administered by intravenous injection for about 1-10 times a month, preferably about 1-5 times a month. The dosage for other parenteral or oral administration may be determined in accordance with the above-described dosage. If the condition is particularly severe, the dosage or the number of administration may be increased according to the condition.

The antibody of the present invention may be administered per se or as an appropriate pharmaceutical composition. A pharmaceutical composition used for the above-described administration comprises the antibody or a salt thereof as well as a pharmacologically-acceptable carrier, diluent or excipient. Such a composition is provided in a formulation appropriate for parenteral or oral administration.

Specifically, examples of compositions for parenteral administration include an injectable agent, nasal drops and a suppository, where the injectable agent includes formulations such as an intravenously-injectable agent, a subcutaneously-injectable agent, intradermally-injectable agent, an intramuscularly injectable agent and an injectable drip. Such an injectable agent is prepared according to a known method, for example, by dissolving, suspending or emulsifying the antibody in a sterile aqueous or oily solution that is generally usable for an injectable agent. For example, physiological saline, glucose, sucrose, mannitol or an isotonic solution containing other adjuvants may be used as an aqueous solution for an injectable agent possibly in conjunction with an appropriate solubilizing aid such as an alcohol (e.g., ethanol), a polyalcohol (e.g., propylene glycol, polyethylene glycol), a non-ionic surfactant [e.g., Polysorbate 80, Polysorbate20, HCO-50 (polyoxyethylene (50 mol) adduct of hydrogenated castor oil)] or the like. For example, sesame oil, soybean oil or the like may be used as an oily solution possibly in conjunction with a solubilizing aid such as benzyl benzoate, benzyl alcohol or the like. The prepared injectable solution is usually packaged in a suitable ampule, vial or syringe. A suppository used for rectal administration may be prepared by mixing the above-described antibody into a usual nasal drop base or suppository base. Moreover, a suitable excipient may be added to the above-described antibody to prepare a lyophilized formulation, which is dissolved in injectable water, physiological saline or the like upon use as an injectable solution. In general, since an oral administration of a protein such as an antibody is believed to be difficult as it is broken down by a digestive organ, oral administration may be possible by devising the antibody fragment or the modified antibody fragment and the formulation thereof.

The above-mentioned parenteral pharmaceutical composition is preferably prepared into a formulation in a dose unit adapted to the dosage of the active element. Examples of such a dose-unit formulation include an injectable agent (an ampule, a vial, a prefilled syringe), nasal drops and suppository, where each dose unit of the formulation preferably contains the above-described antibody for generally 5-500 mg, in particular 5-100 mg for an injectable agent, and 10-250 mg for other formulations.

Each of the above-mentioned composition may contain other active element as long as it does not cause any unfavorable interaction upon compounding with the above-described antibody. For example, a pharmaceutical formulation of the present invention may contain an anti-human α4 integrin antibody in addition to the above-described antibody. In this case, the mixture ratio is not particularly limited but, for example, the ratio of the anti-human α9 integrin antibody to the anti-human α4 integrin antibody may be adjusted within the range of 1:99-99:1.

Diagnostic Agent Comprising Monoclonal Antibody of the Present Invention

A pharmaceutical composition comprising a monoclonal antibody of the present invention may be used as a diagnostic agent for an inflammatory disease such as rheumatoid arthritis or hepatitis, bronchial asthma, fibrosis, diabetes, cancer metastasis, arterial sclerosis, multiple sclerosis or granuloma, or as a diagnostic agent for suppression of chronic rejection after organ transplantation, or for an autoimmune disease such as a systemic autoimmune disease, erythematosus, uveitis, Behcet's disease, polymyositis, proliferative glomerulonephritis or sarcoidosis. Since the monoclonal antibody of the present invention can specifically recognize α9 integrin, it may be used for quantitation of α9 integrin in a test solution, and in particular for quantitation employing sandwich immunoassay, a competition technique, an immunometric technique or the like. No particular condition, procedure or the like is required for adapting each of these immunological determination techniques to a measurement technique of the present invention. The measurement system may be configured by those skilled in the art by applying general technical consideration to usual conditions and procedures for each method. For details of these general technical procedures, reference may be made to articles, documents and the like.

Accordingly, an antibody of the present invention can be used to quantitate α9 integrin in a highly sensitive manner. Furthermore, an antibody of the present invention can be used to quantitate α9 integrin in vivo to diagnose various α9 integrin-related diseases. For example, when an increase or a decrease is detected in the α9 integrin level, diagnosis is that there is a high possibility of suffering or likelihood of suffering an α9 integrin-related disease such as an inflammatory disease. In addition, a monoclonal antibody of the present invention can be used for specifically detecting α9 integrin existing in the subject such as a body fluid or a tissue. It can also be used for preparing an antibody column used for purifying α9 integrin, for detecting α9 integrin contained in each fraction upon purification, or for analyzing the behavior of α9 integrin in a test cell or the like.

Method of Screening for Compound that Inhibits Activity of Human α9 Integrin

An epitope on a human α9 integrin that is recognized by an antibody of the present invention may be utilized to screen for a compound that can inhibit the activity of human α9 integrin. Specifically, the present invention provides a method for screening for a low-molecular compound that inhibits the activity of human α9 integrin, the method comprising using a peptide comprising an amino acid sequence of human α9 integrin (hereinafter, referred to as "peptide A").

According to the screening method of the present invention, for example, comparison is made between (i) a case where peptide A and a ligand of human α9 integrin (for example, tenascin C, plasmin, etc.) are made to contact and (ii) a case where peptide A, the ligand and a test compound are made to contact. The cases (i) and (ii) are compared, for example, by determining binding between the ligand and peptide A. In order to readily compare the bindings, a ligand that has been labeled according to a known technique is preferably used. A candidate compound resulting from such a method is tested to confirm whether or not it inhibits the activity of human α9 integrin, thereby obtaining a compound that inhibits the activity of human α9 integrin.

The test substance used may be a polypeptide, a protein, a non-peptide compound derived from a living organism, a synthetic compound, a microbiological culture, a cell extract, a plant extract, an animal tissue extract or the like, which may be either a novel compound or a known compound.

As is the case with the antibody of the present invention, the selected compound may be used as a prophylactic and/or therapeutic agent for cancers, inflammatory diseases, infectious diseases, autoimmune diseases, bone diseases and the like.

Hereinafter, the present invention will be described in more detail by means of examples below, which do not limit the scope of the present invention.

EXAMPLES

Example 1

Production of Antibody Against Human α9 Integrin

An antibody against human α9 integrin was produced by immunizing three BALB/c mice as follows. First, 3×10⁶ cells/animal of human-α9-integrin-expressing cells (human α9/NIH-3T3 cells) were intraperitoneally administered to the mice, and further 3×10⁶ cells/animal of human α9/NIH-3T3 cells were intraperitoneally administered following one and two weeks. A week later, 2×10⁶ cells/animal of human α9/NIH-3T3 cells were intravenously administered. Clones that reacted with human α9/CHO-K1 cell and human melanoma cell line (G361 cells) endogenously expressing human α9 integrin but that did not react with CHO-K1 cell expressing human α4 integrin were determined as anti-α9-integrin antibodies. As a result, two clones of hybridoma cells (K33N, M35A) that produced anti-human α9 integrin antibody were established.

The thus-obtained hybridoma cells K33N and M35A were each deposited with the International Patent Organism Depositary, the National Institute of Advanced Industrial Science and Technology (Central 6, 1-1-1 Higashi, Tsukuba, Ibaraki, 305-8566) on May 29, 2007, and assigned Accession No. FERM BP-10830 and FERM BP-10831, respectively.

Example 2

Analysis of Complementarity Determining Region (CDR) of Anti-Human α9 Integrin Antibody mRNAs were extracted from hybridomas that produce the human α9 integrin antibodies (K33N, M35A), and subjected to reverse transcription to prepare cDNAs. These cDNAs were used as templates together with ScFv cloning primers (Light Primer Mix, Heavy Primer Mix; Amersham Bioscience) for PCR to elongate and amplify the variable region of each of the heavy and light chains of the antibodies. Subsequently, the PCR products were integrated into pCRII TOPO vectors by a common technique. The resultants were sequenced to determine the amino acid sequences. The above-described procedure was repeated for three times for each antibody.

As a result, the amino acid sequences of the variable regions and the CDR regions of heavy and light chains of K33N and M35A were determined as shown in FIGS. 1A and 1B. Specifically, the amino acid sequences of the CDR regions were as follows.

```
(Heavy chain)
[CDRH1]
                                    (SEQ ID NO: 1)
K33N: SYYMN (SEQ ID NO: 2)
M35A: SYWIH

[CDRH2]
                                    (SEQ ID NO: 3)
K33N: WIFPGSGNTKYNEKFKGK (SEQ ID NO: 4)
M35A: EINPSSGRTNFIENFETK

[CDRH3]
                                    (SEQ ID NO: 5)
K33N: SWVSYERGYYFDY (SEQ ID NO: 6)
M35A: LAYGNYSWFAY (Light chain)
[CDRL1]
                                    (SEQ ID NO: 7)
K33N: RASENIYYSLA (SEQ ID NO: 8)
M35A: RASETVDSYGNTFMH

[CDRL2]
                                    (SEQ ID NO: 9)
K33N: NANSLED (SEQ ID NO: 10)
M35A: LASNLES

[CDRL3]
                                   (SEQ ID NO: 11)
K33N: KQAYDVPYT (SEQ ID NO: 12)
M35A: QQNNEDPYT
```

FIGS. 1A and 1B also show sequences (JN Bio and Takara) obtained by different analysis methods (using different sequence analysis softwares) from the above-described sequence analysis method (GTS). The details of each method are described below.

Sequence Analysis Method by JN Biosciences (K33N)

The hybridoma cell (K33N) was cultured in TIL Media I medium (Immuno-Biological Laboratories) containing 10% fetal bovine serum (FBS; HyClone) under 7.5% $CO_2$ at 37° C. for amplification. Total RNA was extracted from about 3×10⁶ hybridoma cells using TRIzol reagent (Invitrogen) according to the protocol of Invitrogen. Preparation of cDNA by reverse transcription reaction using oligo dT primers was performed with GeneRacer Kit (Invitrogen) according to the protocol provided by Invitrogen. cDNAs of the variable regions of the H- and L-chains were amplified by PCR using 3' primer and GeneRacer 5' primer (5'-CGACTGGAGCACGAGGA-CACTGA-3' (SEQ ID NO:14)) attached to GeneRacer Kit, each corresponding to mouse constant regions γ1 and κ, with Phusion DNA polymerase (New England Biolabs). The 3' primer used for PCR amplification of the H-chain variable region (VH) was 5'-GCCAGTGGATAGACAGATGG-3' (SEQ ID NO:15). The 3' primer used for PCR amplification of the L-chain variable region (VL) was 5'-GATGGATACAGT-TGGTGCAGC-3'(SEQ ID NO:16). The amplified VH and VL cDNAs were subcloned into pCR4Blunt-TOPO vectors (Invitrogen) for sequencing. DNA sequence analyses of the variable regions were carried out with Tocore (Menlo Park).

Sequence Analysis Method by Takara (M35A)

A hybridoma cell (M35A) was cultured and amplified. Then, the total RNA of the cell was extracted using RNAiso (Takara Bio Inc.) according to Acid Guanidine-Phenol-Chloroform method (AGPC method). The extracted RNA was subjected to DNase I treatment according to a common technique, then to phenol chloroform treatment to remove DNase I, and to ethanol precipitation for purification. The resulting RNA was again suspended in distilled water and used for analysis. About 1 μg of DNase-I-treated RNA as a template and Random Primers (9 mer) were used with Reverse Transcriptase M-MLV (RNase H free) for reverse transcription reaction. For PCR amplification of the variable regions, a part of each reverse transcription reactant was used as a template, Heavy Primers 1 and 2 (Amersham Bioscience) for H-chain, Light Primer Mix (Amersham Bioscience) for L-chain, and TaKaRa LA Taq (Takara) as PCR enzyme were used.

The DNA fragment obtained by PCR was subjected to electrophoresis with agarose gel. The band was excised out and the gel was eluted to purify the DNA. The purified DNA was cloned into pMD20-T vector for TA cloning. For DNA sequence analysis of the variable regions, M13-47 primer sequence included in pMD20-T vector was used for gene sequencing. For sequencing reaction, BigDye Terminators v3.1 cycle sequencing kit (Applied Biosystems) was used with ABI3730 sequencer (Applied Biosystems) according to the protocol of the manufacturer.

As can be appreciated from FIGS. 1A and 1B, although there were slight differences in the resulting sequences depending on the analysis method (or the analysis software) employed, there was no difference in the amino acid sequences of CDRs due to different analysis methods.

Example 3

Effect of Anti-Human α9 Integrin Antibody in Inhibiting Cell Adhesion

Since α9 integrin binds to a ligand containing extracellular matrix (ECM) such as OPN, fibronectin, tenascin C and VCAM-1 upon cell adhesion, inhibition of cell adhesion by the resulting novel anti-human α9 integrin antibody was examined as inhibition of binding between an α9-integrin-expressing cell (human melanoma cell G361) and the ligand.

SVVYGLR peptide (SEQ ID NO:18) bound to BSA (bovine serum albumin) was used as OPN peptide, and a protein obtained by expressing the third region of Fibronectin Type III repeat of human tenascin-C in *E. coli* (where RGD sequence within this region was replaced with RAA sequence) was used as TN-C fn3 (RAA).

OPN peptide or tenascin C fragment (TN-C fn3 (RAA)) (5 μg/mL) was left in a 96-well plate at 37° C. for an hour, and then blocked with 0.5% BSA/PBS. The human melanoma cells G361 were prepared to be $1 \times 10^5$ cells/mL with 0.25% BSA/DMEM medium, and added with the anti-human α9 integrin antibody at various concentrations. Two-hundred μL each of the antibody-added G361 cells was placed into a solid-phased 96-well plate and allowed to react at 37° C. for an hour. Washing was repeated twice with PBS and then the adhered cells were immobilized and stained with 0.5% crystal violet/20% methanol. The resultant was washed with distilled water for three times, dissolved in 20% acetic acid and absorbance thereof was determined at 590 nm. Meanwhile, a monoclonal antibody (5A1) against human osteopontin was used as a negative control while five types of anti-human α9 integrin antibodies prepared beforehand (1K11, 21C5, 24I11, 25B6 and 28S1) were used as positive controls.

Effect of the anti-human α9 integrin antibody on adhesion of the G361 cells to OPN peptide is shown in FIG. 2 and the results with tenascin C fragments are shown in FIG. 3.

Similar to negative control 5A1 and positive controls 1K11, 25B6 and 28S1, M35A had less effect in inhibiting cell adhesion of the G361 cells to OPN peptide. On the other hand, K33N inhibited cell adhesion with a smaller amount compared to the positive controls 21C5 and 24I11 and showed an effect of inhibiting cell adhesion to an equal level to that of Y9A2. As to the adhesion of G361 cells to tenascin C fragment, M35A had less effect in inhibiting the cell adhesion while K33N inhibited the cell adhesion with a smaller amount and showed an equal level of inhibition effect to that of Y9A2, in other words, it showed evidently stronger inhibition effect than the positive controls 21C5 and 24I11. Hence, K33N, in particular, exerted particularly remarkable effect in inhibiting cell adhesion as compared to other antibodies.

Example 4

Difference in Recognition Sites of Anti-Human α9 Integrin Antibodies

Since the behavior of newly prepared anti-human α9 integrin antibody K33N in inhibiting cell adhesion was similar to that of Y9A2, competitive reactions of these antibodies to human α9 integrin-expressing cell (hα9/CHO) were detected by FACS to examine the difference in the recognition sites.

To biotin-labeled K33N or Y9A2 (5 μg/mL, 100 μL), 100 times the amount thereof of K33N, Y9A2 or negative control IgG (0.5 mg/mL, 100 μL) was added and then allowed to react with human α9 integrin cells (hα9/CHO, $1 \times 10^7$/mL, 100 μL) (4° C., 30 minutes). The cells were washed with FACS buffer (0.5% BSA/PBS). Streptavidin-labeled APC (0.5 μg/mL, 100 μL) was added to the cell solution for reaction (4° C., 20 minutes). Again, the cells were washed with FACS buffer and the dead cells were stained with 7-AAD (0.05 mg/mL, 20 μL). Subsequently, the cells were again washed with FACS buffer and measured by FACS.

As can be appreciated from FIG. 4, when biotin-labeled Y9A2 and non-labeled Y9A2 were allowed to competitively react with cells expressing human α9 integrin, fluorescence-bound cells were obviously decreased almost to the background level. In the presence of biotin-labeled Y9A2 and non-labeled K33N, however, fluorescence-bound cells were decreased but not as low as the background level. Meanwhile, when biotin-labeled K33N and non-labeled K33N were allowed to compete against each other upon addition to the cells expressing human α9 integrin, fluorescence-bound cells were obviously decreased but fluorescence-bound cells did not decrease upon addition of non-labeled Y9A2 as low as that upon addition of non-labeled K33N. Accordingly, since Y9A2 and K33N did not present complete competition against each other when they would show competition against each other if they recognize the same epitope, Y9A2 and K33N should recognize different epitopes, suggesting that the antibodies were not identical.

Industrial Applicability

The anti-α9-integrin antibody of the present invention shows an excellent effect in suppressing a function of α9 integrin and exerts a therapeutic effect against cancers (for example, cancer cell proliferation or metastasis), inflammatory diseases (for example, rheumatoid arthritis, osteoarthritis, hepatitis, bronchial asthma, fibrosis, diabetes, arterial sclerosis, multiple sclerosis, inflammatory bowel diseases (ulcerative colitis, Crohn's disease, etc.)), infectious diseases (for example, hepatitis), autoimmune diseases (for example, systemic erythematodes, polymyositis, autoimmune thyroid disease, tubulointerstitial nephritis, myasthenia gravis) and bone diseases (for example, osteoporosis) and the like. Moreover, a pharmaceutical composition comprising the anti-α9-integrin antibody of the present invention as well as the anti-α4-integrin antibody exerts an improved therapeutic effect against cancers, inflammatory diseases and the like. The antibody of the present invention may also be utilized as a diagnostic drug since it is capable of pathologically detecting expression of α9 integrin in cells and tissues.

BRIEF DESCRIPTION OF THE DRAWINGS

[FIG. 1A] diagram showing the results from analysis of the amino acid sequence of the variable region containing the complementarity determining region (CDR) of the heavy chain of anti-human α9 integrin antibodies (K33N and M35A). The results shown were obtained by using the GTS sequence analysis method for K33N(SEQ ID NO:20) and M35A (SEQ ID NO:22) and using JN Biosciences sequence analysis method for K33N (SEQ ID NO:21) or Takara sequence analysis method for M35A (SEQ ID NO:23).

[FIG. 1B] A diagram showing the results from analysis of the amino acid sequence of the variable region containing the complementarity determining region (CDR) of the light chain of anti-human α9 integrin antibodies (K33N and M35A). The results shown were obtained by using the GTS sequence analysis method for K33N (SEQ ID NO:24) and M35A (SEQ ID NO:26) and using JN Biosciences sequence analysis method for K33N (SEQ ID NO:25) or Takara sequence analysis method for M35A (SEQ ID NO:27).

SEQUENCE LISTING

Figure 2:
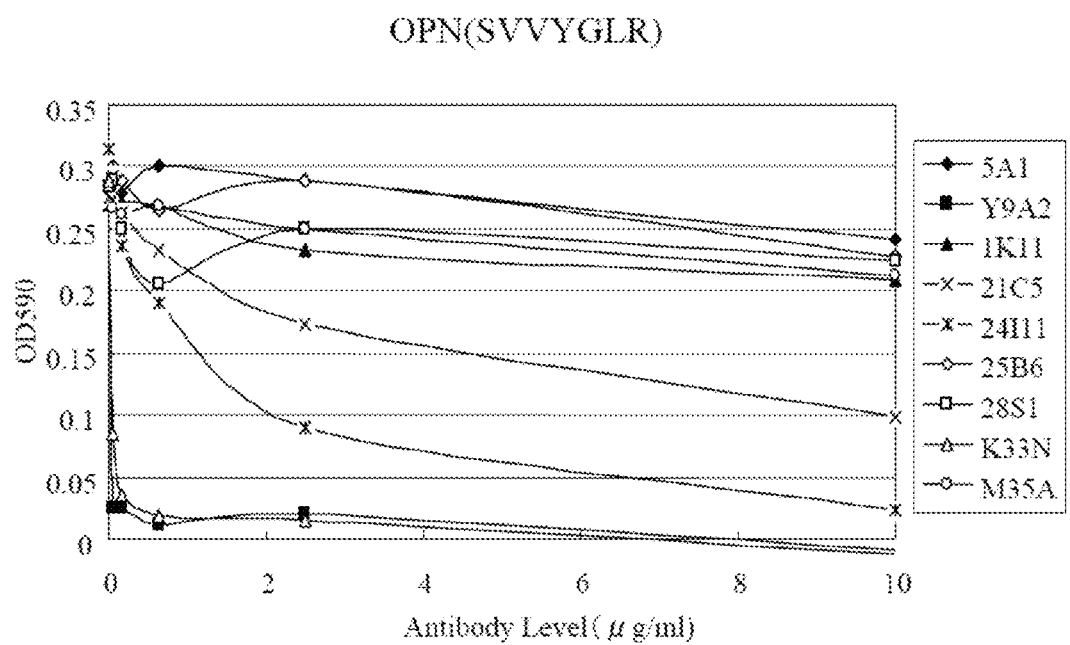
[FIG. 2] A diagram showing the results from examining the effects of anti-human α9 integrin antibodies (two clones of the present invention (K33N, M35A), additional five clones (1K11, 21C5, 24I11, 25B6 and 28S1) and Y9A2) in inhibiting cell adhesion by using a human-α9-integrin-expressing cell (human melanoma cell G361) and an α9-integrin-binding site peptide of OPN (SVVYGLR) (SEQ ID NO:18). A monoclonal antibody against human-osteopontin (5A1) was used as a negative control.
Figure 3:
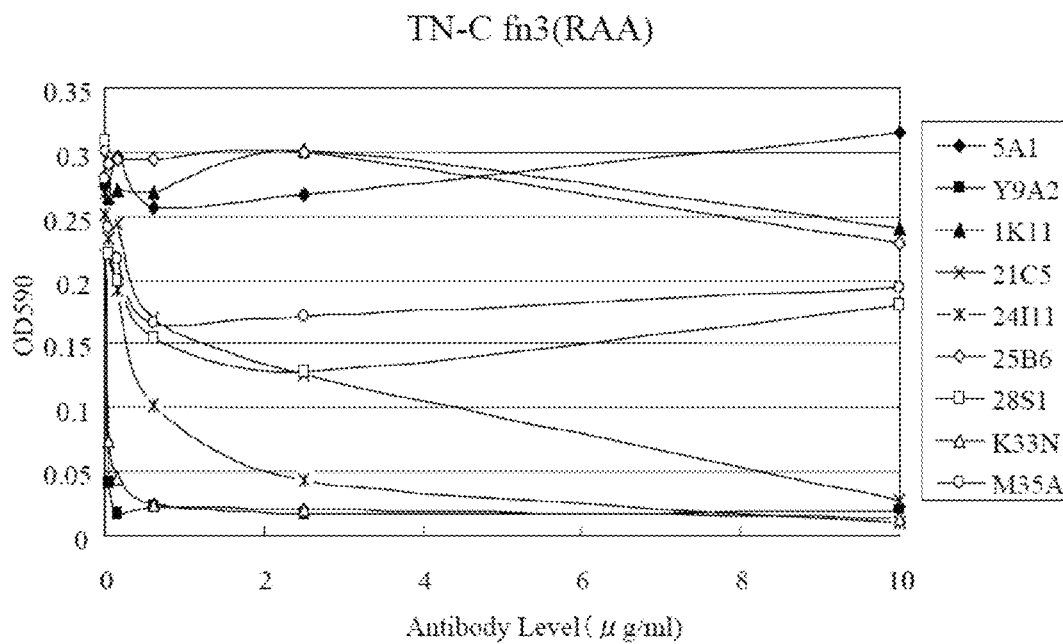
[FIG. 3] A diagram showing the results from examining the effects of anti-human α9 integrin antibodies (two clones of the present invention (K33N, M35A), additional five clones (1K11, 21C5, 24I11, 25B6 and 28S1) and Y9A2) in inhibiting cell adhesion by using a human-α9-integrin-expressing cell (human melanoma cell G361) and an α9-integrin-binding site peptide of tenascin C fragment. A monoclonal antibody against human-osteopontin (5A1) was used as a negative control.
Figure 4:
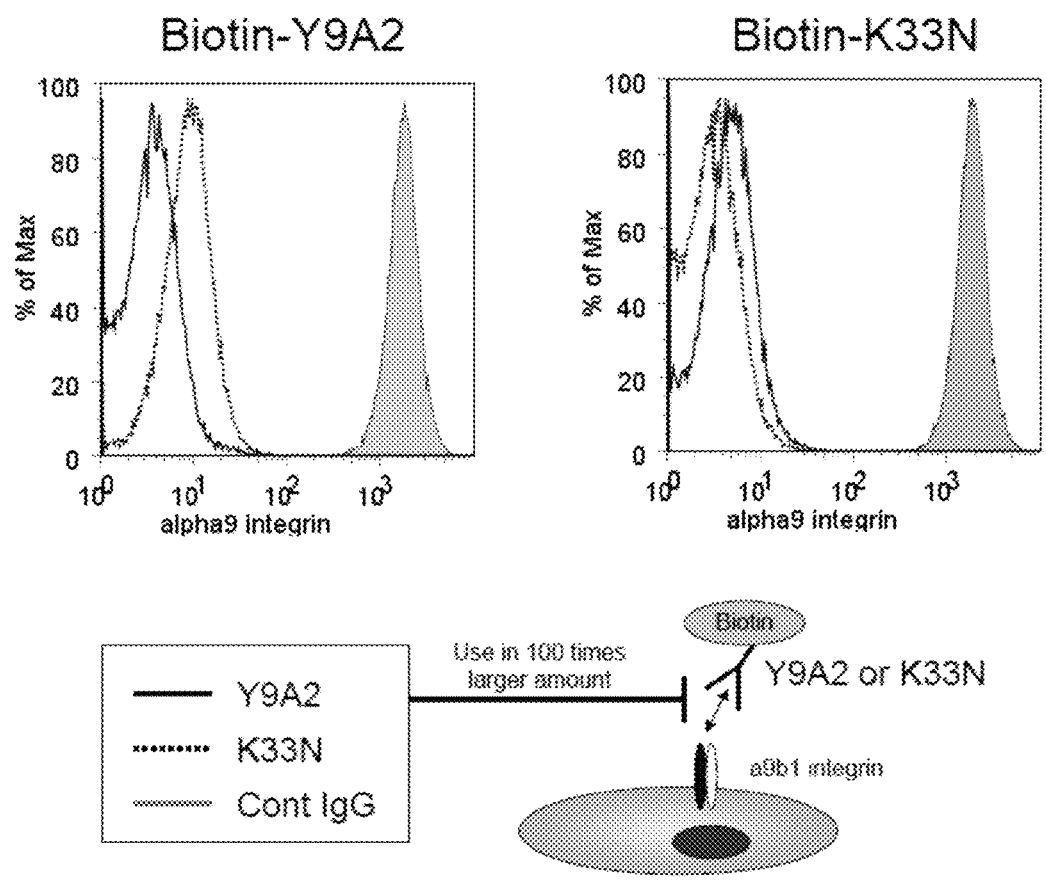
[FIG. 4] A diagram showing the results from examining the competitive reaction of a novel anti-human α9 integrin antibody (K33N) and Y9A2 to a human-α9-integrin-expressing cell.

```
<160> NUMBER OF SEQ ID NOS: 27

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: K33N CDRH1

<400> SEQUENCE: 1

Ser Tyr Tyr Met Asn
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRH1 M35A

<400> SEQUENCE: 2

Ser Tyr Trp Ile His
1               5

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRH2 K33N
```

```
<400> SEQUENCE: 3

Trp Ile Phe Pro Gly Ser Gly Asn Thr Lys Tyr Asn Glu Lys Phe Lys
1               5                   10                  15

Gly Lys

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRH2 M35A

<400> SEQUENCE: 4

Glu Ile Asn Pro Ser Ser Gly Arg Thr Asn Phe Ile Glu Asn Phe Glu
1               5                   10                  15

Thr Lys

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRH3 K33N

<400> SEQUENCE: 5

Ser Trp Val Ser Tyr Glu Arg Gly Tyr Tyr Phe Asp Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRH3 M35A

<400> SEQUENCE: 6

Leu Ala Tyr Gly Asn Tyr Ser Trp Phe Ala Tyr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRL1 K33N

<400> SEQUENCE: 7

Arg Ala Ser Glu Asn Ile Tyr Tyr Ser Leu Ala
1               5                   10

<210> SEQ ID NO 8
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: CDRL1 M35A

<400> SEQUENCE: 8

Arg Ala Ser Glu Thr Val Asp Ser Tyr Gly Asn Thr Phe Met His
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRL2 K33N

<400> SEQUENCE: 9

Asn Ala Asn Ser Leu Glu Asp
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRL2 M35A

<400> SEQUENCE: 10

Leu Ala Ser Asn Leu Glu Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRL3 K33N

<400> SEQUENCE: 11

Lys Gln Ala Tyr Asp Val Pro Tyr Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRL3 M35A

<400> SEQUENCE: 12

Gln Gln Asn Asn Glu Asp Pro Tyr Thr
1               5

<210> SEQ ID NO 13
<211> LENGTH: 1035
<212> TYPE: PRT
```

-continued

<213> ORGANISM: Homo sapiens

<400> SEQUENCE: 13

Met Gly Gly Pro Ala Ala Pro Arg Gly Ala Gly Leu Arg Ala Leu
1               5                   10                  15

Leu Leu Ala Leu Val Val Ala Gly Ile Pro Ala Gly Ala Tyr Asn Leu
            20                  25                  30

Asp Pro Gln Arg Pro Val His Phe Gln Gly Pro Ala Asp Ser Phe Phe
            35                  40                  45

Gly Tyr Ala Val Leu Glu His Phe His Asp Asn Thr Arg Trp Val Leu
        50                  55                  60

Val Gly Ala Pro Lys Ala Asp Ser Lys Tyr Ser Pro Ser Val Lys Ser
65                  70                  75                  80

Pro Gly Ala Val Phe Lys Cys Arg Val His Thr Asn Pro Asp Arg Arg
                85                  90                  95

Cys Thr Glu Leu Asp Met Ala Arg Gly Lys Asn Arg Gly Thr Ser Cys
            100                 105                 110

Gly Lys Thr Cys Arg Glu Asp Arg Asp Asp Glu Trp Met Gly Val Ser
        115                 120                 125

Leu Ala Arg Gln Pro Lys Ala Asp Gly Arg Val Leu Ala Cys Ala His
    130                 135                 140

Arg Trp Lys Asn Ile Tyr Tyr Glu Ala Asp His Ile Leu Pro His Gly
145                 150                 155                 160

Phe Cys Tyr Ile Ile Pro Ser Asn Leu Gln Ala Lys Gly Arg Thr Leu
                165                 170                 175

Ile Pro Cys Tyr Glu Glu Tyr Lys Lys Lys Tyr Gly Glu Glu His Gly
            180                 185                 190

Ser Cys Gln Ala Gly Ile Ala Gly Phe Phe Thr Glu Glu Leu Val Val
        195                 200                 205

Met Gly Ala Pro Gly Ser Phe Tyr Trp Ala Gly Thr Ile Lys Val Leu
    210                 215                 220

Asn Leu Thr Asp Asn Thr Tyr Leu Lys Leu Asn Asp Glu Val Ile Met
225                 230                 235                 240

Asn Arg Arg Tyr Thr Tyr Leu Gly Tyr Ala Val Thr Ala Gly His Phe
                245                 250                 255

Ser His Pro Ser Thr Ile Asp Val Val Gly Gly Ala Pro Gln Asp Lys
            260                 265                 270

Gly Ile Gly Lys Val Tyr Ile Phe Arg Ala Asp Arg Arg Ser Gly Thr
        275                 280                 285

Leu Ile Lys Ile Phe Gln Ala Ser Gly Lys Lys Met Gly Ser Tyr Phe
    290                 295                 300

Gly Ser Ser Leu Cys Ala Val Asp Leu Asn Gly Asp Gly Leu Ser Asp
305                 310                 315                 320

Leu Leu Val Gly Ala Pro Met Phe Ser Glu Ile Arg Asp Glu Gly Gln
                325                 330                 335

Val Thr Val Tyr Ile Asn Arg Gly Asn Gly Ala Leu Glu Glu Gln Leu
            340                 345                 350

Ala Leu Thr Gly Asp Gly Ala Tyr Asn Ala His Phe Gly Glu Ser Ile
        355                 360                 365

Ala Ser Leu Asp Asp Leu Asp Asn Asp Gly Phe Pro Asp Val Ala Ile
    370                 375                 380

Gly Ala Pro Lys Glu Asp Asp Phe Ala Gly Ala Val Tyr Ile Tyr His
385                 390                 395                 400

```
Gly Asp Ala Gly Gly Ile Val Pro Gln Tyr Ser Met Lys Leu Ser Gly
                405                 410                 415
Gln Lys Ile Asn Pro Val Leu Arg Met Phe Gly Gln Ser Ile Ser Gly
            420                 425                 430
Gly Ile Asp Met Asp Gly Asn Gly Tyr Pro Asp Val Thr Val Gly Ala
        435                 440                 445
Phe Met Ser Asp Ser Val Val Leu Leu Arg Ala Arg Pro Val Ile Thr
    450                 455                 460
Val Asp Val Ser Ile Phe Leu Pro Gly Ser Ile Asn Ile Thr Ala Pro
465                 470                 475                 480
Gln Cys His Asp Gly Gln Pro Val Asn Cys Leu Asn Val Thr Thr
                485                 490                 495
Cys Phe Ser Phe His Gly Lys His Val Pro Gly Glu Ile Gly Leu Asn
                500                 505                 510
Tyr Val Leu Met Ala Asp Val Ala Lys Lys Glu Lys Gly Gln Met Pro
            515                 520                 525
Arg Val Tyr Phe Val Leu Leu Gly Glu Thr Met Gly Gln Val Thr Glu
        530                 535                 540
Lys Leu Gln Leu Thr Tyr Met Glu Glu Thr Cys Arg His Tyr Val Ala
545                 550                 555                 560
His Val Lys Arg Arg Val Gln Asp Val Ile Ser Pro Ile Val Phe Glu
                565                 570                 575
Ala Ala Tyr Ser Leu Ser Glu His Val Thr Gly Glu Glu Arg Glu
                580                 585                 590
Leu Pro Pro Leu Thr Pro Val Leu Arg Trp Lys Lys Gly Gln Lys Ile
            595                 600                 605
Ala Gln Lys Asn Gln Thr Val Phe Glu Arg Asn Cys Arg Ser Glu Asp
        610                 615                 620
Cys Ala Ala Asp Leu Gln Leu Gln Gly Lys Leu Leu Leu Ser Ser Met
625                 630                 635                 640
Asp Glu Lys Thr Leu Tyr Leu Ala Leu Gly Ala Val Lys Asn Ile Ser
                645                 650                 655
Leu Asn Ile Ser Ile Ser Asn Leu Gly Asp Asp Ala Tyr Asp Ala Asn
                660                 665                 670
Val Ser Phe Asn Val Ser Arg Glu Leu Phe Phe Ile Asn Met Trp Gln
            675                 680                 685
Lys Glu Glu Met Gly Ile Ser Cys Glu Leu Leu Glu Ser Asp Phe Leu
        690                 695                 700
Lys Cys Ser Val Gly Phe Pro Phe Met Arg Ser Lys Ser Lys Tyr Glu
705                 710                 715                 720
Phe Ser Val Ile Phe Asp Thr Ser His Leu Ser Gly Glu Glu Val
                725                 730                 735
Leu Ser Phe Ile Val Thr Ala Gln Ser Gly Asn Thr Glu Arg Ser Glu
                740                 745                 750
Ser Leu His Asp Asn Thr Leu Val Leu Met Val Pro Leu Met His Glu
            755                 760                 765
Val Asp Thr Ser Ile Thr Gly Ile Met Ser Pro Thr Ser Phe Val Tyr
        770                 775                 780
Gly Glu Ser Val Asp Ala Ala Asn Phe Ile Gln Leu Asp Asp Leu Glu
785                 790                 795                 800
Cys His Phe Gln Pro Ile Asn Ile Thr Leu Gln Val Tyr Asn Thr Gly
                805                 810                 815
Pro Ser Thr Leu Pro Gly Ser Ser Val Ser Ile Ser Phe Pro Asn Arg
```

```
                820                 825                 830
Leu Ser Ser Gly Gly Ala Glu Met Phe His Val Gln Glu Met Val Val
                    835                 840                 845
Gly Gln Glu Lys Gly Asn Cys Ser Phe Gln Lys Asn Pro Thr Pro Cys
    850                 855                 860
Ile Ile Pro Gln Glu Gln Asn Ile Phe His Thr Ile Phe Ala Phe
865                 870                 875                 880
Phe Thr Lys Ser Gly Arg Lys Val Leu Asp Cys Glu Lys Pro Gly Ile
                885                 890                 895
Ser Cys Leu Thr Ala His Cys Asn Phe Ser Ala Leu Ala Lys Glu Glu
                900                 905                 910
Ser Arg Thr Ile Asp Ile Tyr Met Leu Leu Asn Thr Glu Ile Leu Lys
            915                 920                 925
Lys Asp Ser Ser Val Ile Gln Phe Met Ser Arg Ala Lys Val Lys
            930                 935                 940
Val Asp Pro Ala Leu Arg Val Val Glu Ile Ala His Gly Asn Pro Glu
945                 950                 955                 960
Glu Val Thr Val Val Phe Glu Ala Leu His Asn Leu Glu Pro Arg Gly
                965                 970                 975
Tyr Val Val Gly Trp Ile Ile Ala Ile Ser Leu Leu Val Gly Ile Leu
                980                 985                 990
Ile Phe Leu Leu Leu Ala Val Leu  Leu Trp Lys Met Gly Phe Phe Arg
                995                 1000                1005
Arg Arg  Tyr Lys Glu Ile Ile  Glu Ala Glu Lys Asn  Arg Lys Glu
        1010                1015                1020
Asn Glu  Asp Ser Trp Asp Trp  Val Gln Lys Asn Gln
        1025                1030                1035

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgactggagc acgaggacac tga                                           23

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gccagtggat agacagatgg                                               20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gatggataca gttggtgcag c                                             21
```

<210> SEQ ID NO 17
<211> LENGTH: 5
<212> TYPE: PRT
<213> ORGANISM: Unknown
<220> FEATURE:
<223> OTHER INFORMATION: Description of Unknown: OPN cell adhesion
      peptide sequence

<400> SEQUENCE: 17

Gly Arg Gly Asp Ser
1               5

<210> SEQ ID NO 18
<211> LENGTH: 7
<212> TYPE: PRT
<213> ORGANISM: Homo sapiens

<400> SEQUENCE: 18

Ser Val Val Tyr Gly Leu Arg
1               5

<210> SEQ ID NO 19
<211> LENGTH: 7
<212> TYPE: PRT
<213> ORGANISM: Mus sp.

<400> SEQUENCE: 19

Ser Leu Ala Tyr Gly Leu Arg
1               5

<210> SEQ ID NO 20
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Val Lys Leu Gln Glu Ser Gly Pro Glu Leu Val Lys Pro Gly Ala Ser
1               5                   10                  15

Val Lys Ile Ser Cys Lys Ala Ser Gly Tyr Ser Phe Thr Ser Tyr Tyr
                20                  25                  30

Met Asn Trp Val Lys Lys Arg Pro Gly Gln Gly Leu Glu Trp Ile Gly
            35                  40                  45

Trp Ile Phe Pro Gly Ser Gly Asn Thr Lys Tyr Asn Glu Lys Phe Lys
    50                  55                  60

Gly Lys Ala Thr Leu Thr Ala Asp Thr Ser Ser Ser Thr Ala Tyr Met
65                  70                  75                  80

Gln Val Ser Ser Leu Thr Ser Glu Asp Ser Ala Val Tyr Phe Cys Ala
                85                  90                  95

Arg Ser Trp Val Ser Tyr Glu Arg Gly Tyr Tyr Phe Asp Tyr Trp Cys
            100                 105                 110

Gln Gly Thr Thr Leu Thr Val Ser Ser
        115                 120

<210> SEQ ID NO 21
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Tyr Met Asn Trp Val Lys Lys Arg Pro Gly Gln Gly Leu Glu Trp Ile
        35                  40                  45

Gly Trp Ile Phe Pro Gly Ser Gly Asn Thr Lys Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Val Ser Ser Leu Thr Ser Glu Asp Ser Ala Val Tyr Phe Cys
                85                  90                  95

Ala Arg Ser Trp Val Ser Tyr Glu Arg Gly Tyr Tyr Phe Asp Tyr Trp
            100                 105                 110

Gly Gln Gly Thr Ser Leu Thr Val Ser Ser
        115                 120

<210> SEQ ID NO 22
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Val Lys Leu Gln Glu Ser Gly Thr Lys Leu Val Lys Pro Gly Ala Ser
1               5                   10                  15

Val Arg Leu Ser Cys Lys Ala Ser Gly Tyr Thr Phe Thr Ser Tyr Trp
            20                  25                  30

Ile His Trp Val Lys Gln Ser Pro Gly Gln Gly Leu Glu Trp Ile Gly
        35                  40                  45

Glu Ile Asn Pro Ser Ser Gly Arg Thr Asn Phe Ile Glu Asn Phe Glu
    50                  55                  60

Thr Lys Ala Thr Leu Thr Val Asp Arg Ser Ser Thr Thr Ala Tyr Met
65                  70                  75                  80

Gln Leu Thr Ser Leu Thr Ser Glu Asp Ser Ala Val Tyr Tyr Cys Ala
                85                  90                  95

Arg Leu Ala Tyr Gly Asn Tyr Ser Trp Phe Ala Tyr Trp Gly Gln Gly
            100                 105                 110

Thr Thr Val Thr Val Ser Ser
        115

<210> SEQ ID NO 23
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Val Lys Leu Gln Glu Ser Gly Thr Lys Leu Val Lys Pro Gly Ala Ser
1               5                   10                  15

Val Arg Leu Ser Cys Lys Ala Ser Gly Tyr Thr Phe Thr Ser Tyr Trp
            20                  25                  30

```
Ile His Trp Val Lys Gln Ser Pro Gly Gln Gly Leu Glu Trp Ile Gly
            35                  40                  45

Glu Ile Asn Pro Ser Ser Gly Arg Thr Asn Phe Ile Glu Asn Phe Glu
        50                  55                  60

Thr Lys Ala Thr Leu Thr Val Asp Arg Ser Ser Thr Thr Ala Tyr Met
 65                  70                  75                  80

Gln Leu Thr Ser Leu Thr Ser Glu Asp Ser Ala Val Tyr Tyr Cys Ala
                85                  90                  95

Arg Leu Ala Tyr Gly Asn Tyr Ser Trp Phe Ala Tyr Trp Gly Gln Gly
                    100                 105                 110

Thr Thr Val Thr Val Ser Ser
            115

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Ser Pro Ala Ser Leu Ala Ala Ser Val Gly
 1               5                  10                  15

Glu Thr Val Thr Leu Thr Cys Arg Ala Ser Glu Asn Ile Tyr Tyr Ser
                20                  25                  30

Leu Ala Trp Tyr Gln Gln Lys Gln Gly Lys Ser Pro Gln Leu Leu Ile
            35                  40                  45

Tyr Asn Ala Asn Ser Leu Glu Asp Gly Val Pro Ser Arg Phe Ser Gly
        50                  55                  60

Ser Gly Ser Gly Thr Gln Tyr Ser Met Lys Ile Asn Ser Met Gln Pro
 65                  70                  75                  80

Glu Asp Thr Ala Thr Tyr Phe Cys Lys Gln Ala Tyr Asp Val Pro Tyr
                85                  90                  95

Thr Phe Gly Gly Gly Thr Lys Leu Glu Leu Lys
                100                 105

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Gln Met Thr Gln Ser Pro Ala Ser Leu Ala Ala Ser Val Gly
 1               5                  10                  15

Glu Thr Val Thr Leu Thr Cys Arg Ala Ser Glu Asn Ile Tyr Tyr Ser
                20                  25                  30

Leu Ala Trp Tyr Gln Gln Lys Gln Gly Lys Ser Pro Gln Leu Leu Ile
            35                  40                  45

Tyr Asn Ala Asn Ser Leu Glu Asp Gly Val Pro Ser Arg Phe Ser Gly
        50                  55                  60

Ser Gly Ser Gly Thr Gln Tyr Ser Met Lys Ile Asn Ser Met Gln Pro
 65                  70                  75                  80

Glu Asp Thr Ala Thr Tyr Phe Cys Lys Gln Ala Tyr Asp Val Pro Tyr
                85                  90                  95
```

```
Thr Phe Gly Gly Gly Thr Lys Leu Glu Ile Lys
            100                 105

<210> SEQ ID NO 26
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Ile Val Leu Thr Gln Ser Pro Ala Ser Leu Ala Val Ser Leu Gly
1               5                   10                  15

Gln Arg Ala Thr Ile Ser Cys Arg Ala Ser Glu Thr Val Asp Ser Tyr
            20                  25                  30

Gly Asn Thr Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Val
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Asn Trp Lys Asn Gly Arg
            100                 105                 110

<210> SEQ ID NO 27
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Thr Val Asp Ser Tyr
            20                  25                  30

Gly Asn Thr Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Val
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys Arg
            100                 105                 110
```

The invention claimed is:

1. A therapeutic agent for a cancer rheumatoid arthritis, osteoarthritis or hepatitis, comprising as an active component an anti-human α9 integrin antibody comprising the amino acid sequences of SEQ ID NOS:1, 3, and 5 as CDRH1, CDRH2, and CDRH3, respectively, of the complementary determining region of the heavy chain (CDRH), and the amino acid sequences of SEQ ID NOS: 7, 9 and 11 as CDRL1, CDRL2, and CDRL3, respectively, of the complementary determining region of the light chain (CDRL).

2. A therapeutic agent for a cancer, rheumatoid arthritis, osteoarthritis or hepatitis, comprising as active components an anti-human α4 integrin antibody and an anti-human α9 integrin antibody comprising the amino acid sequences represented by SEQ ID NOS:1, 3, and 5 as CDRH1, CDRH2, and CDRH3, respectively, of the complementary determining region of the heavy chain (CDRH), and the amino acid sequences of SEQ ID NOS: 7, 9 and 11 as CDRL1, CDRL2, and CDRL3, respectively, of the complementary determining region of the light chain (CDRL).

3. A diagnostic agent for a cancer, rheumatoid arthritis, osteoarthritis or hepatitis, comprising as an active component an anti-human α9 integrin antibody comprising the amino acid sequences of SEQ ID NOS:1, 3, and 5 as CDRH1, CDRH2, and CDRH3, respectively, of the complementary determining region of the heavy chain (CDRH), and the amino acid sequences of SEQ ID NOS: 7, 9 and 11 as CDRL1, CDRL2, and CDRL3, respectively, of the complementary determining region of the light chain (CDRL).

4. A pharmaceutical composition comprising as an active component an anti-human α9 integrin antibody comprising the amino acid sequences of SEQ ID NOS:1, 3, and 5 as CDRH1, CDRH2, and CDRH3, respectively, of the complementary determining region of the heavy chain (CDRH), and the amino acid sequences of SEQ ID NOS: 7, 9 and 11 as CDRL1, CDRL2, and CDRL3, respectively, of the complementary determining region of the light chain (CDRL) and a pharmacologically-acceptable carrier, diluent or excipient.

5. A method for treating an ECM-related disease, said method comprising administering to a subject in need thereof an anti-human α9 integrin antibody comprising the amino acid sequences of SEQ ID NOS:1, 3, and 5 as CDRH1, CDRH2, and CDRH3, respectively, of the complementary determining region of the heavy chain (CDRH), and the amino acid sequences of SEQ ID NOS: 7, 9 and 11 as CDRL1, CDRL2, and CDRL3, respectively, of the complementary determining region of the light chain (CDRL), wherein said ECM-related disease is selected from the group consisting of rheumatoid arthritis, osteoarthritis and hepatitis.

* * * * *